(12) United States Patent
Tucker

(10) Patent No.: US 7,276,468 B1
(45) Date of Patent: *Oct. 2, 2007

(54) GRANULATED DECONTAMINATION FORMULATIONS

(75) Inventor: Mark D. Tucker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/740,317

(22) Filed: Dec. 18, 2003

Related U.S. Application Data

(63) Continuation-in-part of application No. 09/607,586, filed on Jun. 29, 2000, now Pat. No. 6,566,574, which is a continuation-in-part of application No. 09/109,235, filed on Jun. 30, 1998, now abandoned, application No. 10/740,317, which is a continuation-in-part of application No. 09/952,940, filed on Sep. 14, 2001, now Pat. No. 6,723,890, which is a continuation-in-part of application No. 09/607,586, application No. 10/740,317, which is a continuation-in-part of application No. 10/251,569, filed on Sep. 20, 2002, application No. 10/740,317, which is a continuation-in-part of application No. 10/623,370, filed on Jul. 18, 2003.

(60) Provisional application No. 60/446,642, filed on Feb. 10, 2003, provisional application No. 60/397,424, filed on Jul. 19, 2002, provisional application No. 60/387,104, filed on Jun. 7, 2002, provisional application No. 60/334,271, filed on Nov. 30, 2001, provisional application No. 60/326,508, filed on Oct. 1, 2001, provisional application No. 60/146,432, filed on Jul. 29, 1999.

(51) Int. Cl.
*A62D 3/00* (2006.01)
*B01F 17/18* (2006.01)
*B01F 17/38* (2006.01)
*C11D 1/62* (2006.01)
*C11D 3/39* (2006.01)

(52) U.S. Cl. ............ 510/110; 510/372; 510/504; 588/315; 588/320; 588/400; 588/401; 588/406; 588/408; 588/409; 588/901; 252/186.38; 252/186.41; 252/186.42; 252/186.39

(58) Field of Classification Search ............... 588/200, 588/218, 901; 252/186.38, 186.39, 186.41; 510/110, 370, 372, 504; 516/15
See application file for complete search history.

(56) References Cited

U.S. PATENT DOCUMENTS

| 3,852,210 | A | * | 12/1974 | Krezanoski | ............ 510/372 |
| 3,901,819 | A | * | 8/1975 | Nakagawa et al. | ...... 252/186.4 |
| 4,536,314 | A | * | 8/1985 | Hardy et al. | ............ 510/376 |
| 4,756,845 | A | | 7/1988 | Sugawara et al. | |
| 4,853,143 | A | * | 8/1989 | Hardy et al. | ............ 510/312 |
| 6,245,957 | B1 | * | 6/2001 | Wagner et al. | ............ 588/316 |
| 6,448,062 | B1 | * | 9/2002 | Huth et al. | ............ 435/264 |
| 6,566,574 | B1 | * | 5/2003 | Tadros et al. | ......... 252/186.41 |
| 6,569,353 | B1 | | 5/2003 | Giletto et al. | |
| 6,723,890 | B2 | * | 4/2004 | Tucker et al. | ............ 588/318 |

FOREIGN PATENT DOCUMENTS

WO   WO 02/02192 A1 *   1/2002

* cited by examiner

*Primary Examiner*—Joseph D. Anthony
(74) *Attorney, Agent, or Firm*—Robert D. Watson

(57) ABSTRACT

A decontamination formulation and method of making that neutralizes the adverse health effects of both chemical and biological compounds, especially chemical warfare (CW) and biological warfare (BW) agents, and toxic industrial chemicals. The formulation provides solubilizing compounds that serve to effectively render the chemical and biological compounds, particularly CW and BW compounds, susceptible to attack, and at least one reactive compound that serves to attack (and detoxify or kill) the compound. The formulation includes at least one solubilizing agent, a reactive compound, a sorbent additive, and water. A highly adsorbent sorbent additive (e.g., amorphous silica, sorbitol, mannitol, etc.) is used to "dry out" one or more liquid ingredients into a dry, free-flowing powder that has an extended shelf life, and is more convenient to handle and mix in the field.

8 Claims, No Drawings

GRANULATED DECONTAMINATION FORMULATIONS

CROSS-REFERENCE TO RELATED APPLICATIONS

This application is a continuation-in-part application of U.S. patent application Ser. No. 09/607,586, entitled "*Formulations for Neutralization of Chemical and Biological Toxants*", filed on Jun. 29, 2000, now U.S. Pat. No. 6,566,574, which was a continuation-in-part application of U.S. patent application Ser. No. 09/109,235, entitled "*Aqueous Foams for Mitigation and Decontamination of Chemical and Biological Weapons Agents*", filed on Jun. 30, 1998, now abandoned, and which claimed the benefit of the filing of U.S. Provisional Patent Application Ser. No. 60/146,432, filed on Jul. 29, 1999, and the specifications thereof are incorporated herein by reference.

This application is also a continuation-in-part application of U.S. patent application Ser. No. 09/952,940, entitled "*Concentrated Formulations and Methods for Neutralizing Chemical and Biological Toxants*", filed on Sep. 14, 2001 now U.S. Pat. No. 6,723,890, which is a continuation-in-part application of U.S. patent application Ser. No. 09/607,586, entitled "*Formulations for Neutralization of Chemical and Biological Toxants*", filed on Jun. 29, 2000, now U.S. Pat. No. 6,566,574, and the specifications thereof are incorporated herein by reference.

This application is also a continuation-in-part application of U.S. patent application Ser. No. 10/251,569, entitled "*Enhanced Formulations for Neutralization of Chemical, Biological and Industrial Toxants*", filed on Sep. 20, 2002 now pending, which claimed the benefit of the filing of U.S. Provisional Patent Application Ser. No. 60/326,508, entitled "*DF-200—An Enhanced Formulation for Decontamination and Mitigation of CBW Agents and Biological Pathogens*", filed on Oct. 1, 2001, and of U.S. Provisional Patent Application Ser. No. 60/334,271, entitled "*Configurations for the Rapid Deployment of DF-200*", filed on Nov. 30, 2001, and of U.S. Provisional Patent Application Ser. No. 60/387,104, entitled "*Decontamination Formulations*", filed on Jun. 7, 2002, and the specifications thereof are incorporated herein by reference.

This application is also a continuation-in-part application of U.S. patent application Ser. No. 10/623,370, entitled "*Decontamination Formulation with Sorbent Additive*", filed on Jul. 18, 2003 now pending, which claimed the benefit of the filing of U.S. Provisional Patent Application Ser. No. 60/397,424 entitled "*Powdered Additive for DF-200,*" filed on Jul. 19, 2002, and the specifications thereof are incorporated herein by reference.

This application claims the benefit of the filing of U.S. Provisional Patent Application Ser. No. 60/446,642 entitled "*DF-200 Configurations for Special Applications*", filed on Feb. 10, 2003, and the specification thereof is incorporated herein by reference.

GOVERNMENT RIGHTS

The Government has rights to this invention pursuant to Contract No. DE-AC04-94AL85000 awarded by the U.S. Department of Energy.

BACKGROUND OF THE INVENTION

The present invention relates to formulations for neutralization of chemical, biological and industrial toxants, and methods of making same.

The present invention is directed to materials and methods for neutralization of toxic chemical, biological and industrial compounds or agents, especially chemical and biological weapons agents, and methods of making same. In particular, the present invention is directed to aqueous formulations containing solubilizing compounds, reactive compounds, and sorbent additives that allow the formulation to be pre-mixed and pre-packaged as a multi-part kit system, where one or more of the parts are packaged in a powdered, granulated form for ease of handling and mixing in the field. The aqueous decontamination formulations can be delivered in a wide variety of embodiments, including, but not limited to: foams, sprays, liquids, gels, fogs and aerosols.

Much of the background of decontamination formulations has been previously discussed in the related patent applications and patent listed above. Briefly, the formulations of the present invention fall generally into two families, designated "DF-100" and "DF-200." DF-100 formulations comprise, for example, a cationic surfactant (e.g., benzalkonium chloride) and a reactive compound (e.g., hydrogen peroxide mixed with potassium bicarbonate, which forms the highly reactive, negatively-charged nucleophillic species, hydroperoxycarbonate ($HCO_4^-$), which is a strong oxidant), that when mixed with water (e.g., tap water, well water, seawater, etc.) and exposed to a toxant, neutralizes that toxant. The solubilizing agent serves to effectively render the toxant susceptible to attack, while the reactive compound serves to attack and neutralize the toxant.

The second family of decontamination formulations, DF-200, is an enhanced version of DF-100. In DF-200, a bleaching activator (e.g., propylene glycol diacetate, glycerol diacetate) has been added to speed up reaction kinetics, improve performance, and eliminate the need for pH adjustment.

In both DF-100 and DF-200 decontamination formulations some of the ingredients must be stored separately in order to prevent premature chemical reaction before use. For example, hydrogen peroxide must be stored separately from the other ingredients prior to use, due to its high reactivity. This can be accomplished by packaging the formulation as a multi-part kit system (i.e., 2-part, 3-part or 4-part kits). For example, a two-part kit system can be used, comprising a relatively inert component (Part A), and an active component (Part B) that comprises the reactive compound. The bulk of the make-up water may be "pre-packaged" in one of the two containers, which allows for rapid deployment of the decontamination solution, without the need for providing extra water in the field. Alternatively, the make-up water (including seawater) can be provided in the field, which greatly reduces the weight of the pre-packaged kit components, making it easier to ship and store.

Ideally, all of the various components/parts of a multi-part kit system would be in the form of a dry, granulated, freely flowing powder that can be easily mixed with water that has been provided in the field. Such a dry powder material could be packaged with a desiccant for providing superior moisture protection, thereby extending the shelf life. Fortunately, one of the preferred reactive compounds, hydrogen peroxide, is available in a variety solid, granulated, water-soluble forms, including: urea hydrogen peroxide, sodium perborate, and sodium percarbonate. Preferably, the made-up decontamination solution ideally should be used within 8-24 hours after being made-up in order to have the maximum neutralization effect.

Most of the other ingredients that are used in DF-100/200 (e.g., cationic surfactants, cationic hydrotropes, solvents, peroxide activators, free point depressants, etc.) are typically available only in liquid form. Therefore, a need exists to identify suitable sorbent materials that can used to "dry-out" the liquid ingredients and convert them into a dry, granulated, freely-flowing powder that is more easily handled and mixed in the field, without affecting the neutralization performance of the made-up (i.e., "activated") decontamination solution.

A granulated decontamination formulation would have the following advantages over an all-liquid or part-liquid plus part-granulated formulations:
1. Significant reduction in the weight of the formulation required to be shipped and stored.
2. Saltwater or other low quality water can be used as the make-up water.
3. The formulation can be stored in low temperature locations.
4. Increased shelf life due to removal of water from the formulation.

Against this background, the present invention was developed.

SUMMARY OF THE INVENTION

A decontamination formulation and method of making that neutralizes the adverse health effects of both chemical and biological compounds, especially chemical warfare (CW) and biological warfare (BW) agents, and toxic industrial chemicals. The formulation provides solubilizing compounds that serve to effectively render the chemical and biological compounds, particularly CW and BW compounds, susceptible to attack, and at least one reactive compound that serves to attack (and detoxify or kill) the compound. The formulation includes at least one solubilizing agent, a reactive compound, a sorbent additive, and water. A highly adsorbent sorbent additive (e.g., amorphous silica, sorbitol, mannitol, etc.) is used to "dry out" one or more liquid ingredients into a dry, free-flowing powder that has an extended shelf life, and is more convenient to handle and mix in the field.

DETAILED DESCRIPTION OF THE INVENTION

The present invention addresses the need for a general formulation that neutralizes the adverse effects of either (or both) chemical toxants (including toxic industrial chemicals) and biological toxants, where a toxant is defined as any chemical or biological compound, constituent, substance, species, or agent that through its chemical or biological action on life processes can, if left untreated, cause death, temporary incapacitation, or permanent harm to humans or animals. This includes all such chemicals or biological agents, regardless of their origin or of their method of production, and regardless of whether they are produced in facilities, in munitions, or elsewhere. Neutralization is defined as the mitigation, de-toxification, decontamination, or otherwise destruction of toxants to the extent that the toxants no longer cause acute adverse effects to humans or animals. The formulation and described variations of the present invention can neutralize, and does not itself contain or produce, infection, significant adverse health effects, or even fatality in animals.

An important subset of chemical and biological compounds that the present invention addresses is that of chemical warfare ("CW") and biological warfare ("BW") agents. However, the present invention also addresses toxants that can cause potential adverse health effects to animals, including humans, where such adverse health effects include infections, acute and chronic health effects, and fatalities. Such toxants can be found in an agricultural facility, animal or dairy farm, or food products processing or packaging facility. Additionally, the present invention addresses the need for such a formulation that is itself non-toxic and non-corrosive, and that can be delivered by a variety of means and in different phases.

The word "formulation" is defined herein as the made-up, activated product or solution (e.g., aqueous decontamination solution) that is applied to a surface or body, or dispersed into the air, etc. for the purpose of neutralization, with or without the addition of a gas (e.g., air) to create foam. Unless otherwise specifically stated, the concentrations, constituents, or components listed herein are relative to the weight percentage of the made-up aqueous decontamination solution. The word "water" is defined herein to broadly include: pure water, tap water, well water, waste water, deionized water, demineralized water, saltwater, or any other liquid consisting primarily of $H_2O$.

A minimum set of ingredients for an aqueous decontamination solution comprising a sorbent additive, according to the present invention, may comprise:
a solubilizing compound selected from the group consisting of a cationic surfactant, a cationic hydrotrope, and a fatty alcohol comprising 8-20 carbon atoms;
a reactive compound selected from the group consisting of nucleophilic compounds and oxidizing compounds;
a sorbent additive; and
water.

The solubilizing agent serves to effectively render the toxant susceptible to attack, while the reactive compound serves to attack and neutralize the toxant. The sorbent additive is used to "dry-out" some or all of the liquid ingredients, for use in a pre-packaged, multi-part kit system.

Some examples of suitable cationic surfactants include: quaternary ammonium salts and polymeric quaternary salts. Examples of suitable quaternary ammonium salts include: cetyltrimethyl ammonium bromide, benzalkonium chloride, benzethonium chloride, cetylpyridinium chloride, alkyldimethylbenzylammonium salt, and tetrabutyl ammonium bromide. A preferred cationic surfactant is VARIQUAT 80MC™ (which used to be supplied by WITCO, Inc., but now is supplied by Degussa Goldschmidt). VARIQUAT 80MC™ comprises a mixture of benzyl (C12-C16) alkyldimethylammonium chlorides. A preferred concentration of quaternary ammonium salt used in these decontamination formulations is greater than about 0.1%, but no more than about 10%, because at higher concentrations the quaternary ammonium salt becomes significantly toxic to humans and the environment.

Examples of suitable reactive compounds include: peroxide compounds, activated peroxide compounds (e.g., hydrogen peroxide+bicarbonate), hydrogen peroxide, urea hydrogen peroxide, hydroperoxycarbonate, sodium perborate, sodium percarbonate, sodium carbonate perhydrate, sodium peroxysilicate, sodium peroxypyrophosphate, sodium peroxysilicate, sodium peroxysilicatehydrogen, peroxide adducts of pyrophosphates, citrates, sodium sulfate, urea, sodium silicate, peracetic acid, oximates (e.g., butane-2,3-dione, monooximate ion, and benzohydroxamate), alkoxides (e.g., methoxide and ethoxide), aryloxides (e.g., aryl substituted benzenesulfonates), aldehydes (e.g., glutaraldehyde), peroxymonosulfate, Fenton's reagent (a mixture of iron and peroxide), and sodium hypochlorite.

Use of these reactive compounds in the present invention can produce a variety of negatively-charged nucleophiles, e.g., hydroxyl ions (OH⁻) and hydroperoxide ions (OOH⁻) produced when using hydrogen peroxide; and/or hydroperoxycarbonate ions ($HCO_4^-$) produced when hydrogen peroxide is combined with a carbonate salt. Hydroperoxycarbonate ions ($HCO_4^-$) are a much stronger oxidant than hydroxyl ions (OH⁻) or hydroperoxide ions (OOH⁻), and are especially effective in reacting with biological toxants. When using hydrogen peroxide in some embodiments of the present invention, its concentration is preferably less than about 10%, because higher concentrations are significantly corrosive, especially in the range of 30-50%.

As mentioned above, the reactive compound may comprise hydroperoxycarbonate ions ($HCO_4^-$), which are produced when hydrogen peroxide is combined with a carbonate salt in an aqueous solution. Examples of suitable carbonate salts include: potassium carbonate, potassium bicarbonate, sodium carbonate, sodium bicarbonate, sodium percarbonate ammonium bicarbonate, ammonium hydrogen bicarbonate, lithium bicarbonate, ammonium carbonate, and calcium carbonate. Addition of carbonate salts can also buffer the formulation to optimize the pH.

Sorbent Material Added to "Dry Out" Liquid Ingredients

According to the present invention, a sorbent additive is used to "dry out" one or more liquid ingredients of the aqueous decontamination formulation when pre-packaged in a multi-part kit system. A goal of "drying out" as many liquid ingredients as possible is to produce a dry, free-flowing, granulated powder or powders that can be placed in protective packaging (e.g., with a desiccant), have an extended shelf life, be more convenient to handle and mix in the field (as compared to handling and mixing a liquid), preferably not leave a residue, and have a reduced storage weight. In this way, the sorbent material acts as a drying agent to produce a granulated form.

The process of "drying out" liquid ingredients is not really an evaporation process as it is commonly understood. Rather, the sorbent additive absorbs and/or adsorbs the liquid to produce a powdered, free-flowing, granulated product that is easier to handle. Preferably, the sorbent additive should not contain any water, since some of the liquid ingredients will hydrolyze or degrade in the presence of moisture. Also, the sorbent additive preferably should be water-soluble, so that it can be rapidly dissolved and mixed, and it should leave no residue.

Alternatively, a water-insoluble sorbent additive may be used (e.g., amorphous silica), depending on the application, if the presence of insoluble particles in the formulation is acceptable or desirable. For example, insoluble sorbent particles may be used to thicken and increase the viscosity of the made-up decontamination solution, effectively creating a gel that has increased "hang-time" on vertical surfaces. Alternatively, insoluble sorbent additives may be used as a cleaning solution and/or where an abrasive effect is desired. For some methods of application the presence of a sludge at the bottom of a container may not be a problem. However, the presence of insoluble sorbent particles in the made-up decontamination formulation may damage a pump mechanism, clog a spray nozzle, or leave an undesirable residue.

The sorbent additive is preferably finely ground to a small particle size so that a large effective surface area can be provided for adsorbing/absorbing the liquid ingredient(s). The sorbent additive preferably is chemically compatible with the entire family of DF-100/200 formulations, and should not cause degradation of the decontamination solution's effectiveness, or degrade the foaming properties (if a foaming version is being used). The sorbent additive may be selected from elements/ingredients already found in the decontamination formulation. The sorbent additive may comprise a single compound, or a blend of different compounds. For example, in some foaming embodiments of DF-200, polyethylene glycol (e.g., PEG 8000 or Carbowax 8000) is used as a viscosity builder for the foam. Since PEG 8000 is typically provided as a fine powder and is essentially anhydrous, then it can also serve as some (or all) of the sorbent additive for "drying out" liquid ingredients.

Some examples of suitable compounds that may be used as the sorbent additive, either alone or in various combinations, according to the present invention, are listed in Table 1.

TABLE 1

| Sorbent Additives |
| --- |
| Sodium carbonate |
| Sodium bicarbonate |
| Potassium carbonate |
| Potassium bicarbonate |
| Calcium carbonate |
| Potassium silicate |
| Precipitated silicates |
| Percarbonates |
| Amorphous silica (fumed silica) |
| Sodium Citrate |
| Dendritic Salt (e.g., sea salt) |
| Citric Acid |
| Polyethylene Glycols, (e.g., PEG 8000) |
| Urea |
| Polyols (e.g., Sorbitol, Mannitol) |

Some examples of suitable polyols that may be used as a sorbent additive are listed in Table 2.

TABLE 2

| Polyol Sorbent Additives |
| --- |
| Sorbitol, |
| Mannitol, |
| Hydrogenated Starch Hydrolysates (HSH), |
| Maltitol, |
| Zylitol, |
| Lactitol Monohydrate, |
| Anhydrous Isomalt, |
| Erythritol, and |
| Polydextrose. |

The polyols listed above are sugar-free sweeteners. They are carbohydrates, but they are not sugars. Chemically, polyols are considered polyhydric alcohols or "sugar alcohols" because part of the structure resembles sugar and part is similar to alcohols. However, these sugar-free sweeteners are neither sugars nor alcohols, as those words are commonly used. They are derived from carbohydrates whose carbonyl group (e.g., aldehyde or ketone, reducing sugar) has been reduced to a primary or secondary hydroxyl group.

The most widely used polyols in the food industry are sorbitol, mannitol, and malitol. Sorbitol is derived from glucose; mannitol from fructose; and malitol from high maltose corn syrup. Sorbogem™ and Mannogem™ are product names for sorbitol and mannitol sold by SPI Polyols, Inc., which are available in a wide range of particle size, down to fine sizes (i.e., Sorbogem Fines™).

Sorbitol is a hexahydric alcohol ($C_6H_{14}O_6$) corresponding to glucose, and has a molecular weight of 182.2. It occurs naturally, and can be produced by the hydrogenation of glucose syrup in the presence of Raney Nickel Catalyst. Some synonyms for sorbitol include: cholaxine, clucitol, diakarmon, gulitol, l-gulitol, karion, nivitin, sionit, sorbicolan, sorbite, d-sorbitol, sorbo, sorbol, sorbostyl, sorvilande. Sorbitol has a CAS No. 50-70-4 and an EC No. 200-061-5.

Alternatively, the sorbent additive may be selected to be a "G.R.A.S." material, meaning that it is Generally Accepted As Safe to be used in this and other applications.

Alternatively, the sorbent additive may comprise amorphous silica (i.e., fumed silica). Amorphous silica, which is water-insoluble, is commercially available from the Cabot Corporation under the trade name CAB-O-SIL® in a wide variety of particle sizes, surface areas, bulk densities, and pour densities. CAB-O-SIL® powders are untreated, high-purity, amorphous fumed silicas manufactured by high temperature hydrolysis of chlorosilanes in a hydrogen/oxygen flame. They have extremely small particle sizes, enormous surface areas (from 130-380 m$^2$/g), and can form three-dimensional branched chain aggregates with a length of approximately 0.2-0.3 microns. Further agglomeration takes place during manufacturing to yield a fine, white fluffy powder with an agglomerate size of less than about 44 microns (325 US Mesh).

When amorphous silica is used as a sorbent additive in granulated DF-100/200 decontamination formulations, the dispersed amorphous silica can create a gel, which helps to increase the contact time. Amorphous silica is chemically un-reactive in DF-100/200 formulations, and, thus, does not change its performance against chemical and biological agents when used at relatively low concentrations.

Bleaching Activators

One reason for the improved performance of DF-200 formulations over DF-100 is the addition of a bleaching activator (e.g., propylene glycol diacetate). Bleaching activators can be compounds with O- or N-bounded acetyl groups or with nitrile groups that react with the strongly nucleophilic hydroperoxy anion (OOH$^-$) to yield peroxygenated species, which are more efficient oxidizers than hydrogen peroxide alone.

Since the 1950's, a number of different bleaching activators have been used in commercial laundry detergents, as well as other commercial products. The most common activators are tetraacetyl ethylenediamine (TAED), which is primarily used in Europe and Asia; and n-nonanoyloxybenzenesulfonate (NOBS), which is primarily used in the United States; and N-acetyl pentaacetate. NOBS is a proprietary chemical of the Proctor and Gamble Company. In a laundry detergent, hydrogen peroxide is provided in a solid form (usually as sodium perborate, which reacts in water to form the hydroperoxy anion). The addition of a bleaching activator greatly enhances the ability of a laundry detergent to remove stains from clothing.

It should be noted that TAED and NOBS bleaching activators are extremely insoluble in water (e.g., TAED is only 0.1% soluble at 25° C.). To get around this problem in a laundry detergent, the solid TAED or NOBS particles are kept in suspension by the agitating action of the washing machine, where they slowly react with the hydrogen peroxide in the detergent. However, agitating DF-200 in the field presents practical problems; hence, a water-soluble bleaching activator is preferred.

Some examples of suitable water-soluble bleaching activators, according to the present invention, include: short-chained organic compounds that contain an ester bond (e.g., ethylene glycol diacetate), propylene glycol monomethyl ether acetate, methyl acetate, dimethyl glutarate, diethylene glycol monoethyl ether acetate, glycerol acetate (monoacetin), glycerol diacetate (diacetin), glycerol triacetate (triacetin), acetylcholine chloride, 4-cyanobenzoic acid, and propylene glycol diacetate. A preferred water-soluble bleaching activator is propylene glycol diacetate (PGDA), which is shown below.

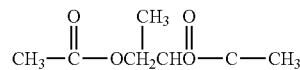

This molecule reacts with hydroperoxy anions OOH$^-$), giving up the ester bonds to form two peroxygenated molecules.

Propylene glycol diacetate (PGDA) also acts as an organic solvent that is highly effective in solubilizing insoluble organic molecules (e.g., chemical warfare agents, as well as foam stabilizers/boosters (such as 1-dodecanol and Lauramide DEA). Therefore, an added function of this compound is that it can be used to supplement the diethylene glycol monobutyl ether (DEGMBE) solvent that may be used in DF-100 and DF-100A formulations, or to supplement the di(propylene glycol) methyl ether solvent that may be used in some DF-200 formulations, thereby allowing the propylene glycol diacetate to serve a dual purpose (i.e., solvent and bleaching activator).

Bleaching activators are generally not stable in water for long periods of time. This is especially true when the aqueous solution is at a high pH (>10). Therefore, for long shelf life, the propylene glycol diacetate (or other bleaching activator) is preferably stored separate from the aqueous solution until use. This is not unlike other products that utilize bleach activators (e.g., laundry detergents), where all the components of the formulation are kept dry and separated until use (note: in the case of laundry detergent, the bleaching activator is encapsulated to prevent it from reacting with the peroxide component until both components are mixed in water).

Another example of a water-soluble bleaching activator is ethylene glycol diacetate, which also works well in DF-200 formulations. However, when ethylene glycol diacetate reacts with hydrogen peroxide it forms ethylene glycol (i.e., anti-freeze), which is a relatively toxic byproduct. Propylene glycol diacetate, on the other hand, does not form this relatively toxic byproduct.

Solid O-acetyl bleaching activators (e.g., acetylcholine chloride, which is often used in eye drop solutions) may be used in Granulated DF-100/200 formulations in place of (liquid) propylene glycol diacetate. The chemical structure of this O-acetyl bleaching activator is shown below.

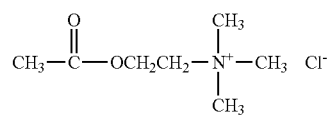

As can be seen, the molecule contains an O-acetyl group that can activate peroxide, and it is a quaternary compound, which is very compatible with Granulated DF-100/200 formulations. Acetylcholine chloride is also soluble in water, and is very hygroscopic.

Three other O-acetyl bleaching activators, monoacetin (glycerol monoacetate) diacetin (glycerol diacetate), and triacetin (glycerol triacetate) have also been tested for their effectiveness in DF-200 formulations. All of these compounds have also proven to be extremely effective bleaching activators. These compounds are water-soluble liquids.

Experiments have also shown that the peroxide in DF-200 formulations is also effectively activated by a nitrile-containing compound, such as 4-cyanobenzoic acid (which is water-soluble), at a concentration of, for example, 2%, for the neutralization of both chemical agent and biological agent simulants.

Other Ingredients

Granulated DF-100/200 formulations, according to the present invention, may optionally comprise cationic hydrotropes, fatty alcohols and/or a freeze point depressant.

Examples of suitable cationic hydrotropes include: tetrapentyl ammonium bromide, triacetyl methyl ammonium bromide, and tetrabutyl ammonium bromide. A preferred cationic hydrotrope is ADOGEN 477™ (which used to be supplied by WITCO, Inc., but now is supplied by Degussa Goldschmidt). ADOGEN 477™ comprises pentamethyltallow alkyltrimethylenediammonium dichloride.

Examples of suitable fatty alcohols include alcohols having 8-20 carbon atoms per molecule, such as: 1-dodecanol, 1-tridecanol, hexadecanol, and 1-tetradecanol.

Examples of a freeze point depressant include propylene glycol.

Next, we present another example of an aqueous decontamination formulation for use in neutralization of a toxant, according to the present invention (by weight percentage):

Granulated DF-200NF Decontamination Solution With Sorbent Additive 0.1-8% cationic surfactant;
    0-8% cationic hydrotrope;
    2-8% carbonate salt;
    1-4% sorbent additive;
    0-8% bleaching activator;
    0-5% water-soluble polymer;
    1-20% urea hydrogen peroxide;
    0-10% freeze-point depressant; and
    balance water.

In particular, the cationic surfactant may comprise benzalkonium chloride; the carbonate salt may comprise potassium carbonate; the sorbent additive may comprise amorphous silica; the bleaching activator may comprise glycerol diacetate or propylene glycol diacetate; the water-soluble polymer may comprise polyethylene glycol; and the freeze-point depressant may comprise propylene glycol.

In general, for any DF-100/200 formulation, a buffer may be added to the made-up decontamination solution, or to one of the Part A or Part B components, in order to adjust the final pH of the solution. Buffer compounds may include, for example: KOH, citric acid, and HCL. Alternatively, sodium bisulfate (a common pool conditioning chemical), or other acid, can be used in place of citric acid to adjust the pH.

Next, we present an example of a non-foaming decontamination formulation, DF-200NF, where the sorbent additive comprises amorphous silica (e.g., CAB-O-SIL®), according to the present invention that is pre-packaged as a three-part kit system.

Granulated Formulation for DF-200NF Using Amorphous Silica Sorbent Additive

Part A (Granulated):
    30 g Variquat 80MC (cationic surfactant)
    55 g Potassium Carbonate (carbonate salt)
    20 g Polyethylene Glycol 8000 (water-soluble polymer)
    30 g CAB-O-SIL® M-5 Powder (sorbent additive)
    20 g Glycerol Diacetate or Propylene Glycol Diacetate (bleaching activator)

Part B (Granulated Oxidant Component):
    85 g Urea Hydrogen Peroxide (reactive compound)

Part C (Water Component):
    660-760 g Water
    0-100 g Propylene Glycol (freeze-point depressant)
    (Note: total mass of Part C should be 760 g)

This formulation will produce 1000 g of decontamination solution (Part A and Part B comprise 24% of the weight of the final formulation). Preferably, the pH of the final formulation should be between 9.6 and 9.85 for optimal decontamination of all target agents. To prepare this formulation, the following procedure may be used: Combine Part A and Part B. Mix Part A/B into Part C. After mixing, use preferably within 8 hours, but preferably not longer than 24 hours.

The performance of granulated DF-200NF with amorphous silica sorbent additive, in the configuration shown above, for neutralization of chemical agent simulants is given in Table 3 below:

TABLE 3

Reaction rates in kinetic testing for the granulated DF-200NF formulation.

| | % Decontaminated | | |
|---|---|---|---|
| Simulant | 1 Minute | 15 Minutes | 60 Minutes |
| Mustard (HD) | 89 | Not Detected | Not Detected |
| VX | 13 | 96 | >99 |

Tests against the anthrax spore simulant (*Bacillus globigii* spores) demonstrated 99.9999% (7- log) kill after a 60 minute exposure to the granulated DF-200NF formulation. When preparing the formulation for use, the two granulated components (urea hydrogen peroxide [Part B] and the CAB-O-SIL blend [Part A]) may be mixed together before being mixed with the water (Part C). However, Parts A and B must be packaged and stored separately due to the high reactivity of the urea hydrogen peroxide.

The use of amorphous silica in DF-100/200 formulations makes it a gel. This allows the formulation to be deployed as a 'high hang time' gel through equipment such as commercially available paint sprayers or military decontamination sprayers. To check this, the formulation described above was sprayed onto a plastic tarp that was hung in a vertical position. The surface of the tarp remained wet for over 30 minutes.

It is also important to note that at concentrations of CAB-O-SIL over approximately 4% (by weight) in the formulation shown above, the amorphous silica sorbent additive begins to inhibit the chemical reactions with chemical simulants. Therefore, it is important to keep the concentration of this ingredient as low as possible, while still maintaining good gelling properties (if desired) and good free flowing powder properties of the granulated components. Also, it should be noted that the CAB-O-SIL sorbent additive is insoluble in water and is actually suspended in the DF-200NF formulation (after addition of water), rather than being dissolved.

Next, we present an example of a high-strength, non-foaming decontamination formulation, "High Strength DF-200NF," using amorphous silica (e.g., CAB-O-SIL®), according to the present invention that is pre-packaged as a three-part kit system. Here, the make-up water is assumed to already be present in a drum, barrel, vessel, etc. that contains a suspected, possibly unknown, chemical or biological agent. Both Parts A and B can be easily carried by a soldier, first responder, firefighter, etc. and then simply tossed into the drum containing suspected CBW agent. The package containing granulated Part A and/or Part B may be made of a water-dissolvable material. Alternatively, the package can be opened and the contents simply poured into the vessel.

Granulated Formulation for High Strength DF-200NF Using Sorbent Additive
Part A (Granulated):
    40 g Variquat 80MC (cationic surfactant)
    55 g Potassium Carbonate (carbonate salt)
    20 g Polyethylene Glycol 8000 (water-soluble polymer)
    20 g CAB-O-SIL® M-5 Powder (amorphous silica sorbent additive)
    40 g Glycerol Diacetate or Propylene Glycol Diacetate (bleaching activator)
Part B (Granulated Oxidant Component):
    135 g Urea Hydrogen Peroxide (reactive compound)

Note: Parts A and B should be added to a batch reactor or other vessel (e.g., drum, barrel) containing water and the suspected chemical or biological agent. Parts A and B shown above should be added to approximately 700 g of water/CBW solution to make-up about 1000 grams total. Parts A and B comprise about 30% of the weight of the final formulation. The pH of the made-up solution preferably should be between about 9.6 and about 9.85.

A first example of a method for preparing a granulated Part A:
1. Place the Variquat 80MC (cationic surfactant) and bleaching activator (propylene glycol diacetate or glycerol diacetate) in a mixing vessel.
2. While mixing, slowly add the Potassium Carbonate.
3. While mixing, slowly add the Polyethylene Glycol 8000.
4. While mixing slowly add the CAB-O-SIL sorbent additive until a free flowing powder is achieved.
5. Store in an enclosed container with a moisture barrier or desiccant.

A second example of a method for preparing a granulated Part A is:
1. Place the CAB-O-SIL sorbent additive in a mixing vessel.
2. While mixing, slowly add the Variquat 80MC.
3. While mixing, slowly add the bleaching activator (propylene glycol diacetate or glycerol diacetate).
4. While mixing, slowly add the Potassium Carbonate.
5. While mixing, slowly add the Polyethylene Glycol 8000 until a free-flowing powder is achieved.
6. Store in an enclosed container with a moisture barrier or desiccant.

In another example, a granulated formulation for DF-200NF with Sorbent Additive may have the following composition ranges; wherein for every 1000 grams of aqueous decontamination formulation made-up after mixing Parts A and B with water:

Part A (Granulated) comprises:
    5-80 grams of cationic surfactant;
    20-80 grams of carbonate salt;
    10-40 grams of sorbent additive;
    0-80 grams of bleaching activator; and
    0-50 grams of water-soluble polymer; and
Part B (Granulated) comprises:
    10-200 grams of urea hydrogen peroxide.

Next, we present an example of a non-foaming, granulated decontamination formulation, DF-200NF, where the sorbent additive comprises amorphous silica (e.g., CAB-O-SIL®), according to the present invention. Here, the formulation is pre-packaged as a two-part kit system: a granulated Part A and a liquid Part B.

Granulated Formulation for DF-200NF Using Amorphous Silica Sorbent (Two-Part Kit)
Part A (Granulated):
    30 g Variquat 80MC (cationic surfactant)
    55 g Potassium Carbonate (carbonate salt)
    20 g Polyethylene Glycol 8000 (water-soluble polymer)
    30 g CAB-O-SIL® M-5 Powder (sorbent additive)
    20 g Glycerol Diacetate or Propylene Glycol Diacetate (bleaching activator)
Part B (Granulated Oxidant Component):
    845 g Hydrogen Peroxide solution, 4.5% concentration (reactive compound)

This formulation will produce 1000 g of decontamination solution. The pH of the final solution should be adjusted to be in-between about 9.6 and 9.85. To prepare this formulation, mix Part A into Part B.

This two-part configuration may be packaged in a spray bottle, where the liquid peroxide component (Part B) is stored in the bottle; and the dry, granulated component (Part A) is added to the spray bottle and mixed together when the formulation is to be used. In this way, the formulation could be used for decontaminating small volumes (e.g., to decontaminate a letter containing a suspicious powder).

Next, we present an example of a foaming, granulated decontamination formulation using amorphous silica (e.g., CAB-O-SIL®), according to the present invention that is pre-packaged as a three-part kit system.

Granulated Formulation for Foaming DF-200 Using Water-Soluble Sorbent Additive
Part A (Granulated):
    20 g Variquat 80MC (cationic surfactant)
    5 g Adogen 477 (cationic hydrotrope)
    12 g Hexylene Glycol (solvent)
    4 g 1-Dodecanol (fatty alcohol)
    130 g Sorbigem (water-soluble sorbent additive)
    48 g Potassium Carbonate (carbonate salt)
    2.5 g Potassium Bicarbonate (carbonate salt)
    20 g Diacetin (bleaching activator)
    5 g Poly(Ethylene Glycol) 8000 (water-soluble polymer)
Part B (Granulated):
    85 g Urea Hydrogen Peroxide (reactive compound)

For use, add 700 g of water to Parts A and B. Parts A and B represent approximately 32% by weight of the final formulation (with water). The sorbent additive in this example, Sorbigem (which is a trade name for sorbitol polyol), is water-soluble, and converts Part A into a granulated, free-flowing powder. Amorphous silica was not used for the sorbent additive in this example, due to its thickening and gelling properties, which would prevent a stable foam from forming when deployed.

In this example, the concentration of Adogen 477 (cationic hydrotrope) is reduced in order to have less liquid to "dry-out". Also, hexylene glycol is used as a solvent, instead of DEGMBE, DPGME, or propylene glycol because it was found that the hexylene glycol absorbs better onto the Sorbigem sorbent additive. The PEG 8000 concentration is also reduced because Sorbigem adds viscosity to the final solution (after water is added); thus less of the polymer is required to achieve the desired viscosity. A key issue when using Sorbigem (sorbitol) in any formulation is that the granulated components must be kept dry either by the use of airtight packaging or by including dessicants in the package.

In foaming DF-100/200 formulations, a cationic water-soluble polymer (e.g., Jaquar 8000™), can be used to increase the bulk viscosity of the solution and produce a more stable foam. Some examples of other suitable non-anionic water-soluble polymers include: polyvinyl alcohol, guar gum, (cationic or non-ionic) polydiallyl dimethyl ammonium chloride, polyacrylamide, glycerol, poly(ethylene oxide), poly(ethylene glycol), polyethylene glycol 8000 (e.g., PEG 8000), and Jaguar 8000™ (Guar Gum 2-hydroxypropyl ether) and poly-ethoxylated glycerine. A cationic polymer is preferred over a non-ionic polymer because anionic polymers do not work well. Fatty alcohols, i.e., 1-dodecanol, serve to increase the surface viscosity of the foam lamellae and to increase foam stability against drainage and bubble collapse. Other foaming agents may also be included in high-foaming formulations, namely Celquat SD 240c (at about 0.15%) and/or Lumulse POE 12 (at about 4%). Polyethylene glycol polymer (PEG 8000) may be used for viscosity enhancement. This polymer is used in many cosmetics and is extremely soluble and stable in water. In addition, it is easier to mix into solution than Jaguar 8000 or a high molecular weight poly(ethylene oxide), since it does not have the tendency to clump.

Some differences between DF-100 and DF-200 decontamination formulations include:

DF-200 is active against all agents at a single pH. The formulation is effective at pH values between about 7.5 and 10.5; is more effective at pH values between about 9.2 and 9.8; and is most effective at pH values between about pH 9.6 and 9.8;

DF-200 has better performance against Mustard;

DF-200 has better performance against bacterial spores;

DF-200 has lower concentrations of both the cationic surfactant and/or the cationic hydrotrope, which further lowers the (already low) toxicity and corrosivity properties of the formulation;

DF-200 has a lower concentration of a foam stability component, 1-Dodecanol;

DF-200 uses a lower concentration of a short-chained alcohol (e.g., isobutanol, isopropanol), which causes flammability problems when the formulation is packaged in a concentrated form;

Some embodiments of DF-200 don't use Diethylene Glycol MonoButyl Ether (DEGMBE), which can cause false alarms on some chemical agent sensors and detectors (especially older sensors which are used in some military settings); and DF-200 can contain a lower concentration of hydrogen peroxide, which also reduces the (already low) toxicity and corrosivity properties of the formulation.

DF-200 performs optimally at a higher pH (about 9.6 to 9.8) as compared to DF-100A. However, note that this is the typical pH value for common household products such as laundry detergents, shampoos, and dishwashing detergents; and DF-200 has more individual components that should be stored separately (e.g., the hydrogen peroxide and the bleaching activator) from the bulk formulation until use, as compared to DF-100 (where only one component, hydrogen peroxide, should be stored separately).

Next, we present an example of a decontamination kit system comprising two components, that when mixed together with a sufficient amount of water, make an aqueous decontamination formulation for use in neutralization of a toxant, the kit system comprising:

(a) a first premixed, granulated component, Part A, comprising:
  a solubilizing compound selected from the group consisting of a cationic surfactant, a cationic hydrotrope, and a fatty alcohol comprising 8-20 carbon atoms; and
  a sufficient amount of a sorbent additive such that Part A is a freely-flowing, powdered substance; and (b) a second premixed, granulated component, Part B, comprising a reactive compound selected from the group consisting of nucleophilic compounds and oxidizing compounds.

Next, we present an example of a kit system comprising two components, that when mixed together, makes an aqueous decontamination formulation for use in neutralization of a toxant, the kit system comprising:

(a) a first premixed, granulated component, Part A, comprising:
  a solubilizing compound selected from the group consisting of a cationic surfactant, a cationic hydrotrope, and a fatty alcohol comprising 8-20 carbon atoms; and
  a sufficient amount of a sorbent additive such that Part A is a freely-flowing, powdered substance; and (b) a second premixed component, Part B, comprising:
  a reactive compound selected from the group consisting of nucleophilic compounds and oxidizing compounds; and
  water.

When all of the water is "pre-packaged" in either of Part A or Part B, the mixing of the formulation for use can be accomplished in a very short time since it only consists of two parts. Therefore, it could be deployed very rapidly at the scene of an incident involving chemical and biological warfare agents. This configuration is ideal for use the civilian first responder (firefighter, HazMat units, police officers, and others who would be the first to arrive at the location of a CBW attack). However, it is heavier to carry than other configurations that add water in the field.

In general, sodium percarbonate may be used as the source of bicarbonate and as a portion of the peroxide in Part B, instead of using urea hydrogen peroxide. This substitution is useful because sodium percarbonate is much less expensive than urea hydrogen peroxide. However, sodium percarbonate dissolves much more slowly than urea hydrogen peroxide after it has been added to Part A. Hence, to increase the dissolution velocity, sodium percarbonate can be milled to approximately a 100-mesh or smaller size for use in this configuration. The time to dissolve the sodium percarbonate was decreased from approximately 30 minutes to about 2 minutes when milled sodium percarbonate was used.

Corrosion inhibitors may be added to granulated DF-100/200 formulations to reduce their corrosivity. A preferred corrosion inhibitor is N,N-dimethyl ethanolamine. Other corrosion inhibitors, such as triethanolamine, ethanolamine salts of C9, C10, and C12 diacid mixtures, dicyclohexyl amine nitrite, and N,N-dibenzylamine, may also be used. The corrosion inhibitors added to granulated DF-100/200 formulations can serve multiple purposes, including:
1. a corrosion inhibitor,
2. a pH buffer,
3. a solvent to keep 1-dodecanol in solution, and
4. a co-solvent to solubilize insoluble chemical agents, such as sarin or mustard.

In other embodiments of granulated DF-100/200 formulations, glycerol may be employed as a viscosity builder in place of Jaguar 8000, poly (ethylene oxide), or polyethylene glycol. Glycerol (glycerine) is a common ingredient in cosmetics, where it is used a viscosity builder, humectant, and emolient. Thus, the use of glycerol in DF-200 formulations can serve multiple purposes:
1. viscosity builder,
2. a humectant (i.e., a substance which moisturizes the skin),
3. a solvent to keep 1-dedecanol in solution, and
4. a co-solvent to solubilize insoluble chemical agents, such as sarin or mustard.

A drawback to the use of glycerol is that it is solid at a fairly high temperature (below about 10° C.). Therefore, it would preferably be used in controlled temperature conditions (i.e., warm temperature conditions). Alternatively, ethoxylated forms of glycerol [e.g., poly(ethoxylated glycerol)] can be used. These forms of glycerol have a lower freezing point.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents.

The invention claimed is:

1. An aqueous decontamination formulation for use in neutralization of a toxant, said formulation comprising (by weight percentage):

0.5-8% cationic surfactant;

2-8% carbonate or bicarbonate salt;

1-4% sorbent additive selected from the group consisting of dendritic salt (sea salt) and urea, and combinations thereof;

1-8% water soluble bleaching activator selected from the group consisting of short-chained organic compounds that contain an ester bond, ethylene glycol diacetate, propylene glycol monomethyl ether acetate, methyl acetate, dimethyl glutarate, diethylene glycol monoethyl ether acetate, glycerol acetate (monoacetin), glycerol diacetate (diacetin), glycerol triacetate (triacetin), acetylcholine chloride, 4-cyanobenzoic acid, propylene glycol diacetate, and combinations thereof;

0.1-5% water-soluble polymer;

1-20% urea hydrogen peroxide;

0.1-10% freeze-point depressant; and water; wherein:

said cationic surfactant comprises benzalkonium chloride;

said carbonate salt comprises potassium carbonate;

said bleaching activator comprises glycerol diacetate or propylene glycol diacetate;

said water-soluble polymer comprises polyethylene glycol; and said freeze-point depressant comprises propylene glycol.

2. The formulation according to claim 1, further comprising one or more solvents selected from the group consisting of di(propylene glycol) methyl ether, diethylene glycol monobutyl ether, hexylene glycol, N,N-dimethlyethylamine, isobutanol, and isopropanol.

3. The formulation according to claim 1 further comprising one or more corrosion inhibitors selected from the group consisting of N,N-dimethyl ethanolamine, triethanolamine, ethanolamine salts of C9, C10, and C12 diacid mixtures, dicyclohexyl amine nitrite, and N,N-dibenzylamine.

4. The formulation according to claim 1 further comprising a cationic hydrotrope comprising one or more compounds selected from the group consisting of tetrapentyl ammonium bromide, triacetyl methyl ammonium bromide, tetrabutyl ammonium bromide, and pentamethyltallow alkyltrimethylenediammonium dichloride.

5. The formulation according to claim 1, further comprising a buffer for adjusting the pH of said aqueous decontamination formulation.

6. The formulation according to claim 1 further comprising a fatty alcohol comprising one or more compounds selected from the group consisting of 1-dodecanol, 1-tridecanol, hexadecanol, and 1-tetradecanol.

7. The formulation according to claim 1 further comprising glycerol or ethoxylated forms of glycerol.

8. The formulation of claim 1, wherein the final pH of the aqueous decontamination formulation, after mixing, is between approximately 9.6 and approximately 9.85.

* * * * *